US008545387B2

(12) United States Patent
Harrison et al.

(10) Patent No.: US 8,545,387 B2
(45) Date of Patent: Oct. 1, 2013

(54) APPARATUS AND METHOD FOR MINIMALLY INVASIVE IMPLANTATION OF HEART ASSIST DEVICE

(75) Inventors: Lewis Harrison, Arlington, TX (US); Stanley Dean Hall, Colleyville, TX (US); Dennis Robbins, Richardson, TX (US)

(73) Assignee: Corinnova Incorporated, Houston, TX (US)

( * ) Notice: Subject to any disclaimer, the term of this patent is extended or adjusted under 35 U.S.C. 154(b) by 1065 days.

(21) Appl. No.: 12/290,810

(22) Filed: Nov. 4, 2008

(65) Prior Publication Data

US 2009/0118570 A1 May 7, 2009

Related U.S. Application Data

(60) Provisional application No. 61/001,733, filed on Nov. 5, 2007.

(51) Int. Cl.
*A61B 17/00* (2006.01)
(52) U.S. Cl.
USPC .......................................................... 600/37
(58) Field of Classification Search
USPC ........................................... 600/37; 128/898
See application file for complete search history.

(56) References Cited

U.S. PATENT DOCUMENTS

| 7,189,203 | B2 * | 3/2007 | Lau et al. | 600/37 |
| 2005/0010197 | A1 * | 1/2005 | Lau et al. | 606/1 |
| 2005/0055032 | A1 * | 3/2005 | Lau et al. | 606/108 |
| 2005/0137673 | A1 * | 6/2005 | Lau et al. | 607/129 |

* cited by examiner

*Primary Examiner* — Christine Matthews
*Assistant Examiner* — Joshua D Lannu
(74) *Attorney, Agent, or Firm* — Chainey P. Singleton; Edwin S. Flores; Chalker Flores, LLP

(57) ABSTRACT

A method and related apparatus for the minimally invasive implantation about a heart of at least a deployable device such as a heart assist device or cardiac compression device. The method comprises the steps of performing a left thoracotomy or subxiphoid incision; obtaining access to the pericardial sac; making a generally linear incision in the pericardial sac; positioning an assembly having an insertion aperture member with an upper ring and a lower ring or flange and insertion tube having therein a deployable device. The apparatus of the present invention includes an insertion aperture member having an upper ring and a lower ring or flange; and an insertion tube having therein a deployable device adapted to be deployed from the insertion tube inside the pericardial sac via a generally linear incision.

20 Claims, 3 Drawing Sheets

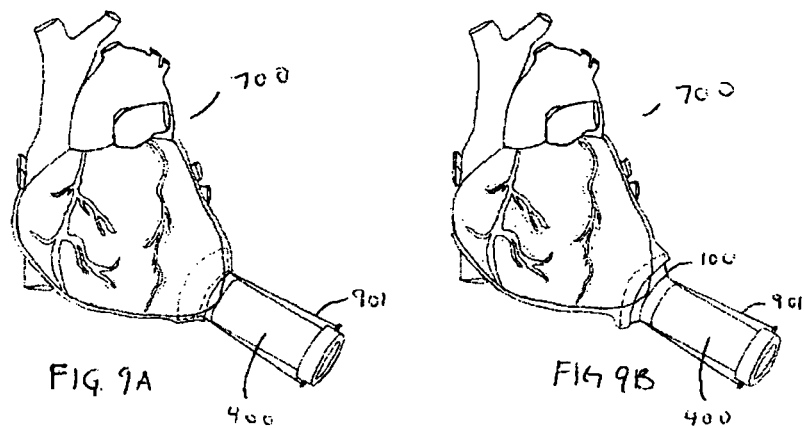
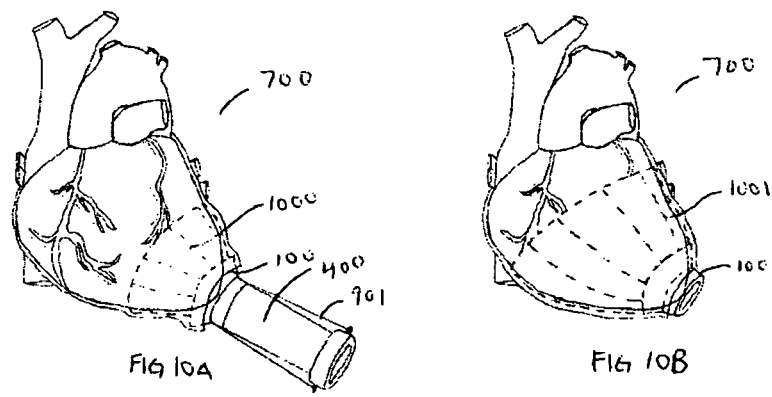

APPARATUS AND METHOD FOR MINIMALLY INVASIVE IMPLANTATION OF HEART ASSIST DEVICE

CROSS REFERENCE TO RELATED APPLICATION

This application claims the benefit of U.S. Provisional Application No. 61/001,733 filed on Nov. 5, 2007, entitled "APPARATUS AND METHOD FOR MINIMALLY INVASIVE IMPLANTATION OF HEART ASSIST DEVICE."

FIELD OF THE INVENTION

The present invention relates to implantation of an assistive biotechnology apparatus, including associated device and method adapted to restore heart function to those who having insufficient cardiac output.

BACKGROUND

The left ventricle is the large, muscular chamber of the heart that pumps blood out to the body. Congestive heart failure (CHF) is a condition in which the heart can't pump enough blood to the body's other organs. It is a complex multi-factorial disease which often begins after an index event such as a severe heart attack which produces an initial decline in pumping capacity of the heart. There are 800,000 people with end-stage CHF and only 2,200 hearts available for transplant each year, leaving a large number of people suffering from this disease. Most CHF patients endure long hospital stays and other medical complications. For people over age 65, it is the number one cause of death, with nearly 290,000 people dying from this disease each year.

Of the 800,000 people who suffer from end-stage heart failure, about 48,000 are suitable for bridge to transplant and 90,000 patients are suitable for destination therapy. Bridge to transplant refers to the use of ventricle assist devices (VADs) to sustain severe heart failure patients until a donor heart becomes available and they can receive a transplant. Destination therapy refers to the use of a left ventricular assist device for long-term therapy. Destination therapy has a larger market potential than the bridge to transplant, however there is only one FDA approved participant in this market.

After the initial decline in pumping capacity of the heart following heart failure, a variety of compensatory mechanisms are activated. The phenomenon of left ventricular remodeling, i.e. a geometrical change in the architecture of the left ventricle, followed by a change in the wall stress is considered the single most important cause for the worsening of these heart attack patients. These patients often drift from Class I to Class IV stage heart failure. Subsequently these patients are rendered helpless and immobile with no options for treatment other than maintenance therapies—and, if the patient is young enough, placement on a cardiac transplant waiting list.

One treatment for patients who suffer from either a myocardial infarction or CHF is the implantation of a direct cardiac compression device. Currently, a sternotomy is the preferred method of implantation of the cardiac compression device. Sternotomy is a type of surgical procedure in which a vertical inline incision is made along the sternum, after which the sternum itself is divided, or "cracked". This procedure provides access to the heart for surgical procedures. Conventional direct cardiac compression devices, such as the Anstadt cup, require a sternotomy for implantation, which is a very painful procedure. Disadvantageously, sternotomies result in long recovery times and a high risk of infection. Further, there is a high risk of complications due to the lengthy surgery required for these unstable patients.

What is desired is a minimally invasive apparatus and associated implantation method adapted to permit the insertion of a cardiac assist device about the heart of a patient which can modulate the end diastolic volume of the left ventricle. End diastolic volume is the volume of blood in a ventricle at the end of filling or diastole. Diastole is the period of time when the heart fills with blood after systole, or contraction. Such an apparatus and method would be preferable over treatment with pharmacological therapies or expensive device therapies.

Current approaches to minimally invasive implantation of heart-assist devices of various types suffer the shortcoming of being relatively slow and difficult procedures, resulting in additional stress on the patient and reducing the likelihood of a favorable outcome. The present invention addresses this shortcoming.

SUMMARY OF THE INVENTION

The following presents a simplified summary of the present invention in order to provide a basic understanding of some aspects thereof. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

The present invention relates to implantation of an assistive biotechnology apparatus adapted to restore heart function to those who are disabled and moribund because of insufficient cardiac output.

The present invention, which includes an insertion aperture member having a flange that is elastically deformable to facilitate insertion through a generally linear incision opening in the pericardial sac, permits the deployment of a deployable device such as a heart assist or cardiac compression device, with a minimally invasive procedure: a left thoracotomy or, alternatively, a subxiphoid incision. The pericardial sac, also referred to as the pericardium, is a conical sac of fibrous tissue which surrounds the heart and the roots of the great blood vessels. The pericardium has outer and inner coats. The outer coat loosely cloaks the heart, and is attached to the central part of the diaphragm and the back of the sternum or breastbone. The inner coat has two layers, with one layer closely adherent to the heart while the other lines the inner surface of the outer coat with the intervening space being filled with fluid. This small amount of fluid, referred to as the pericardial fluid, acts as a lubricant to allow normal heart movement within the chest. The outer layer of the pericardium is called the parietal pericardium. The inner part of the pericardium that closely envelops the heart is called the visceral pericardium or epicardium. A thoracotomy is the process of making of an incision (cut) into the chest wall. The xiphoid refers to inferior end of the sternum that articulates with the sternal body and serves as an attachment point for the diaphragm and abdominal muscles.

The present invention facilitates accelerated implantation versus conventional procedures and devices thus reducing the amount of time a critical patient must spend in surgery. Implantation of an apparatus including a deployable device in accordance with the present invention through a left thoracotomy or subxiphoid incision drastically reduces the recovery time and risk of infection for these patients.

DESCRIPTION OF THE DRAWINGS

A more complete understanding of the present invention may be obtained by reference to the following Detailed Description, when taken in conjunction with the accompanying Drawings, wherein:

FIGS. 9A and 9B are illustrations of (A) an insertion tube of the present invention being attached to the insertion aperture member containing a deployable device, and (B) the insertion tube and insertion device of the present invention being pulled away from the apex of the heart to allow space for the deployable device;

FIGS. 10A and 10B are illustrations of the initial deployment of the deployable device through the insertion aperture member of the present invention and (B) the final placement of the deployable device with the insertion tube of the present invention removed and the insertion aperture member of the present invention left in place.

DETAILED DESCRIPTION

The present invention will now be described more fully with reference to the accompanying drawings, in which preferred embodiments of the present invention are shown. The present invention may, however, be embodied in many different forms and should not be constructed as limited to the embodiments set forth herein; rather, these embodiments are provided so that this disclosure will be thorough and complete, and will fully convey the scope of the present invention to those skilled in the art.

The present invention is directed to a minimally invasive implantation apparatus and method and is adapted to save the lives of CHF patients and dramatically shorten their hospital stays. With the present invention, in combination with drug therapy and an exercise program, many of the patients receiving a deployed device, such as a cardiac compression device, in accordance with the present invention, could have restored cardiac function in as little as three weeks, allowing a shorter hospital stay and increased quality of life.

As noted, direct cardiac compression devices require a sternotomy for implantation. In contrast, the present invention permits at least a deployable device to be implanted using a minimally invasive left thoracotomy or subxiphoid incision, allowing patients to recover within a shorter period, resulting in a shorter hospital stays and less of a chance for infection.

Figure 1:
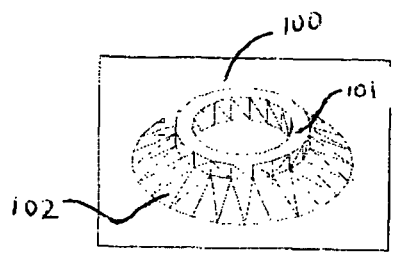
FIG. 1 is an isometric top view of the insertion aperture member of the present invention.

The present invention can be broadly viewed as an assembly comprising an insertion aperture member 100 and an insertion tube 400, alone, together, or in combination with a deployable device, such as a heart assist or cardiac compression device. As seen in FIG. 1, the insertion aperture member 100 further comprises an upper ring 101, and a lower ring or flange 102 made of, for example, silicon, polytetrafluoroethylene (PTFE), ultra high molecular weight polyethylene (UHMWPE), a suitable polymer, elastomer or rubber material. The upper ring 101 is a protruding rim, edge, or collar coupled to the lower ring or flange 102 and adapted to receive the insertion tube. The upper ring 101 of the insertion aperture member 100 is semi-rigid whereas the lower ring or flange 102 is a substantially collapsible portion having a conical shape with a portion thereof which includes the apex removed. The semi-rigidity of the upper ring 101 allows for easier handling during insertion via a left thoracotomy or subxiphoid incision and provides the insertion aperture member 100 with structural strength when placed inside the pericardial space. The lower ring or flange 102 is flexible and collapsible so that it may be inserted via a relatively smaller incision into the pericardial space of a heart. For example, the lower ring or flange 102 preferably has a Shore Durometer A hardness rating in the range of approximately 5 to 50.

The lower ring or flange 102 is generally conical or partially prolate ellipsoidal in shape to fit the natural curvature of the heart. The lower ring or flange 102 is dimensioned such that when it is expanded in the pericardial sac, the lower ring or flange 102 has a greater circumference than the opening in the pericardial sac and therefore cannot be easily pulled through the pericardial opening. Because the pericardial sac is somewhat resilient, the opening, created by a generally linear incision in the pericardium need only be dimensioned so as to receive upper ring 101. More specifically, upper ring 101 of the insertion aperture member 100 can range in diameter from one half inch to three inches and vary in shape, symmetrically and non symmetrically, whereas the lower ring or flange 102 of the insertion aperture member 100 can range in diameter from one inch to five inches and also vary in shape, symmetrically and non symmetrically so as to fit the contour of the heart.

Figure 2:
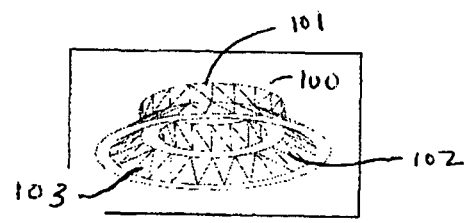
FIG. 2 is an isometric bottom view of the insertion aperture member of the present invention.
Figures 8A, 8B:
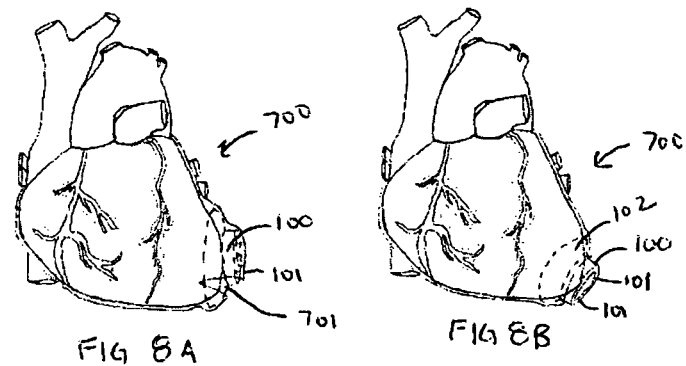
FIGS. 8A and 8B are illustrations of (A) the initial insertion of the aperture member of the present invention into the pericardial space and (B) the final placement of the insertion aperture member of the present invention into the pericardial space.

Once the insertion aperture member 100 is inserted into the pericardial space and positioned correctly, the pericardium can be pulled around the edge of the upper ring 101, binding the insertion aperture member 100 in place. As seen in FIGS. 2, 8A and 8B, the lower ring or flange 102 is generally conical in shape to contour to the natural curvature of the heart, as seen in FIGS. 2 and 8(A) and (B). This shape can be made more or less conical depending on the shape of the heart and amount of force needed to pull the pericardium away from the heart.

Figure 3:
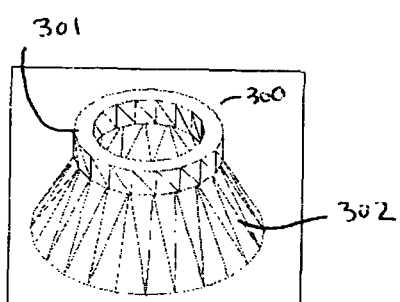
FIG. 3 is an isometric view of an insertion aperture member of the present invention having a more conical shape.

FIG. 3 illustrates an insertion aperture member 300 with a more conical shape, that is the ratio of the height to the base of the lower ring or flange 302, is greater. As seen therein, insertion aperture member 300 has an upper ring 301, and a lower ring or flange 302 made of, for example, silicon, polytetrafluoroethylene (PTFE) and ultra high molecular weight polyethylene (UHMWPE), a suitable polymer, elastomer or rubber material.

Figure 4:
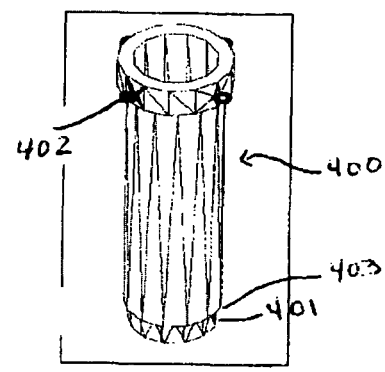
FIG. 4 is an isometric top view of the insertion tube of the present invention.

As seen in FIG. 4, the insertion tube 400 included within the assembly of the present invention is a rigid cylinder having a proximate open end and a distal open end of a predetermined circumference and a cylinderical wall, the rigid cylinder being formed made of a synthetic or semi-synthetic material such as a plastic or polymer, and adapted to receive a deployable device. In operation, the distal open end is nearest the heart when inserted into the chest of a patient.

Proximate the distal open end of insertion tube 400 is a bottom section 401 of the insertion tube 400 having a fitting adapted to be received by an insertion aperture member (not shown in FIG. 4). Above the fitting is a stop 403, such as a ledge, rim or edge portion proximate the distal open end that abuts the top surface of the upper ring of an insertion aperture member when the two are coupled or joined. The insertion tube 400 can be made at various lengths to accommodate the depth of the chest cavity. Further, the insertion tube can be comprised of two or more concentric tubes in which an innermost tube is longer than the outer tubes to allow attachment to be coupled to the insertion aperture member. Further, the insertion tube can have a curvature in the longitudinal direction thereof so as to align the opening of the insertion tube with the apex of the heart. In this manner, the curvature allows for the sub-xiphoid incision and apex of the heart to not be directly aligned. In a further aspect, the insertion tube may be angled at the distal end nearest the apex of the heart so as to allow the incision and the apex to not be directly aligned. Furthermore, the insertion tube may have removable or fixed spade or shoehorn type fixture so as to allow a surgeon to access the space between the pericardium and the heart. Such a shoehorn fixture can be coupled to an existing insertion tube.

Near the proximate end of the insertion tube 400 are four eyelets 402 coupled to an outer circumference thereof that are used to secure the insertion tube 400 to the insertion aperture member. As seen in FIGS. 9A, 9B and 10A, sutures 901 can be coupled to the insertion aperture member 100 and once the insertion tube 400 is positioned, the sutures 901 can be tied to the eyelets 402. The sutures 901 will then bind the insertion tube 400 to the insertion aperture member 100 allowing a surgeon to pull on the insertion tube 400 and create space between the pericardium and the heart without decoupling the insertion aperture member 100 from the insertion tube 400 as seen in FIGS. 9A and 9B. The number of eyelets on the insertion tube can be varied to add stability or reduce the operating time. Several other methods of coupling the insertion tube to the insertion aperture member include, but are not limited to, threaded fittings, snap fittings, channel locking fittings, and press fittings.

Figure 5:
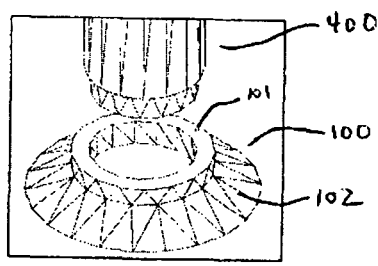
FIG. 5 is an isometric view of the insertion tube being fitted into the insertion aperture member of the present invention.

FIG. 5 is a close up view illustrating the coupling of the insertion tube 400 and insertion aperture member 100. This fitting can be accomplished in several ways as previously mentioned. For example, threaded fittings can be used to join the two pieces together, wherein the insertion tube has male threads and the insertion aperture member has female threads of the same thread count. Snap fittings could also be used, where the insertion tube contains a rigid portion that snaps into the insertion aperture member when pressed together. Alternatively, channel locking fittings can be used wherein a groove is placed inside the upper ring of the insertion aperture member and a notch on the insertion tube. The notch on the insertion tube would be adapted to fit inside the channel and lock into place when turned relative to the insertion aperture member. A further attachment alternative is a pressure fitting whereby the insertion tube is adapted to fit inside the insertion aperture member with the components held together by friction. Further alternatives wherein the insertion tube is coupled to the insertion aperture member include Luer locking fittings, and filament ties.

Figure 6:
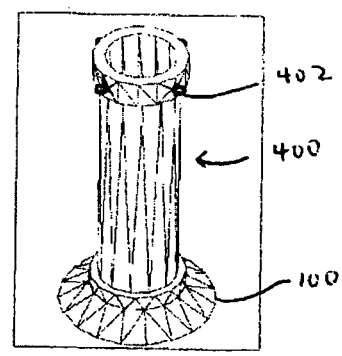
FIG. 6 is an isometric view of the complete assembly of the present invention.

FIG. 6 illustrates the complete assembly 600 of the present invention showing the insertion tube 400 coupled with the insertion aperture member 100 in accordance with the present invention.

Figures 7A, 7B:
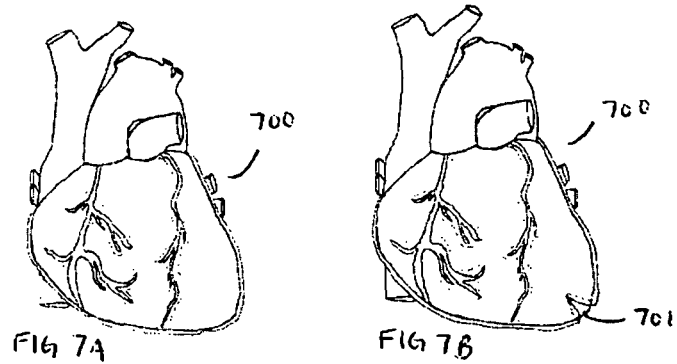
FIGS. 7A and 7B are illustrations of a heart with (A) an intact pericardium and (B) with an opening cut at the apex of the pericardial sac.

A deployable device is implanted about a heart in accordance with the method of the present invention, using the assembly hereinabove described, as follows. A normal left thoracotomy or subxiphoid incision is performed. Referring now to FIGS. 7A and 7B, once access to the pericardial sac 700 has been obtained, a small incision 701 is made in the pericardial sac 700 as hereinbefore described and as seen in FIG. 7B. The insertion aperture member is folded and grasped by long forceps and then inserted inside the pericardial sac. Referring now to FIGS. 8A and 8B, the insertion aperture member 100 is pushed through the incision in the pericardium. The insertion aperture member 100 may be slid completely through the opening in the pericardium along the anterior of the heart wall. Once the insertion aperture member 100 is completely inside the pericardial space, it preferably is slid back toward the apex of the pericardium and the flaps of the opening in the pericardium are pulled around the upper ring 101 of the insertion aperture member 100. The elasticity of the pericardium assist in maintaining the opening and keeping the insertion aperture member 100 in place as seen in FIG. 8B. The insertion tube 400 containing a deployable device such as a heart assist or cardiac compression device, is then coupled to the insertion aperture member 100 as previously disclosed and as seen in FIG. 9A. Once the insertion tube 400 is attached to the insertion aperture member 100, the entire apparatus can be pulled away from the heart to create space between the pericardial sac and the apex of the heart as seen in FIG. 9B. If the opening in the pericardial sac is too large, the insertion aperture member 100 may be pulled out of the opening. Sutures can be used to help hold the insertion aperture member 100 in place if this problem occurs. Once the pericardium is lifted away from the apex of the heart, the deployable device 1000, 1001 such as a heart assist or cardiac compression device may be deployed as seen in FIGS. 10A and 10B. Such an implantable cardiac compression device 1000, 1001 is adapted to be affixed to the wall of a ventricle of a heart and, e.g., to compress the ventricle. The present invention further includes a deploying mechanism adapted to deploy and retract the deployable device through the insertion tube and insertion aperture member.

As noted herein, there are a number of features and advantages of the apparatus and method of the present invention, including: the apparatus is adapted to permit deployment of a deployable device, such as a cardiac compression device, through a small left thoracic incision or subxiphoid incision; the apparatus further permits deployment of a deployable device such as a heart assist or cardiac compression device into the pericardial space inside the pericardial sac via a small incision located at the apex of the pericardium; the insertion aperture member of the apparatus of the present invention being collapsible to fit inside the pericardial opening and then expand to a dimension greater than that of the opening; the apparatus being adapted to stabilize the pericardial sac without the need for suturing—however, suturing may be incorporated during the implantation procedure; the apparatus comprising a minimal number of components—including an insertion aperture member which stabilizes the pericardial sac and an insertion tube which houses a deployable device and is adapted to guide the deployable device during deployment; and the insertion aperture member and insertion tube being separated or integrated into a single unit. Once in place, the apparatus of the present invention allows a surgeon to lift the pericardial sac away from the apex of the heart in order to gain space required for deployment of a deployable device—there is no need for suturing to accomplish this task, although suturing may be applied. If the two components of the apparatus of the present invention are separate components, once the insertion aperture member is in place, it can be attached to the insertion tube containing the deployable device and after the attachment of the insertion tube to the insertion aperture member, the deployable device may be deployed around the heart under the pericardial sac. After deployment of the deployable device, the insertion tube may be removed from the insertion aperture member. Further, the insertion aperture member may be removed or may be left in place to allow for future access to the pericardial space. The apparatus of the present invention is made of biocompatible materials including from the group including, but not limited to silicon, polytetrafluoroethylene (PTFE), ultra high molecular weight polyethylene (UHMWPE), a suitable polymer, elastomer or rubber material and may be coated with therapeutic agents, drugs or substances to assist in healing.

The embodiments shown and described above are only exemplary. Even though numerous characteristics and advantages of the preferred embodiments of the present invention have been set forth in the foregoing description together with details of the invention, the disclosure is illustrative only and changes may be made within the principles of the invention to the full extent indicated by the broad general meaning of the terms used in the attached claims.

We claim:

1. A method for a minimally invasive implantation in a heart of a deployable device comprising the steps of:
    performing one of a left thoracotomy or subxiphoid incision;
    obtaining access to a pericardial sac;
    making a generally linear incision in the pericardial sac dimensioned to receive an insertion aperture member, wherein the insertion aperture member comprises an upper aperture within a generally circular outer edge and a lower flange connected to the insertion aperture member;
    positioning the generally circular outer edge inside the pericardial sac against an inner surface of the pericardial sac through the generally linear incision;
    extending the lower flange through the generally linear incision to extend outside the pericardial sac;
    removably coupling an insertion tube to the lower flange to align the hollow insertion tube and the upper aperture ring to form a hollow channel for the insertion of a deployable device;
    moving the insertion aperture member against the inner surface of the pericardial sac to separate the pericardial sac from the heart; and
    deploying the deployable device from the insertion tube inside the pericardial sac.

2. The method of claim 1, further comprising the step of preloading the deployable device inside the insertion tube.

3. The method of claim 1, further comprising the step of removing the insertion tube from the insertion aperture member after deployment of the deployable device.

4. An apparatus adapted to facilitate deployment of a deployable cardiac device comprising:
    an insertion aperture member having an upper aperture ring with a generally circular outer edge, wherein the generally circular outer edge is adapted to be positioned inside a pericardial sac via a generally linear incision in the pericardial sac and the generally circular outer edge is adapted to be positioned against a pericardial sac inner surface,
    a lower flange connected to the insertion aperture member to extend outside the generally linear incision in the pericardial sac; and
    an insertion tube adapted to removably couple to the lower flange and align with the upper aperture ring to form a passage into the pericardial sac;
    wherein the lower flange is elastically deformable and configured to be inserted through the generally linear incision in the pericardial sac.

5. The apparatus of claim 4, further comprising a deployable device adapted to fit within the insertion tube and capable of being deployed inside the pericardial sac.

6. The apparatus of claim 4, wherein the insertion tube has a length such that it can be pulled so as to cause the pericardial sac to be pulled from a surface of the heart to allow insertion of the deployable device inside the pericardial sac via the generally linear incision.

7. The apparatus of claim 4, wherein the insertion tube has a curvature in a longitudinal direction thereof so as to align an opening of the insertion tube with the apex of a heart.

8. The apparatus of claim 4, wherein the insertion tube has an angled end on a distal end nearest the apex of the heart so as to allow the incision and the apex to not be directly aligned.

9. The apparatus of claim 4, wherein the insertion tube includes a shoehorn type fixture to allow a surgeon to access a space between the pericardial sac and the heart.

10. The apparatus of claim 9, wherein the shoehorn type fixture is coupled to the insertion tube.

11. The apparatus of claim 4, wherein the insertion aperture member is made from one of the group consisting of silicon, polytetrafluoroethylene (PTFE), ultra high molecular weight polyethylene (UHMWPE), a polymer, elastomer and rubber material.

12. The apparatus of claim 11, wherein the lower flange has an elastomeric hardness of about 5 to 50 on the Shore Durometer A hardness rating scale.

13. The apparatus of claim 4, wherein the insertion tube is made from one of the group consisting of silicon, polytetrafluoroethylene (PTFE), ultra high molecular weight polyethylene (UHMWPE), a suitable polymer, elastomer and rubber material.

14. The apparatus of claim 4, wherein the insertion tube is coupled to the insertion aperture member using a locking mechanism from the group consisting of a threaded fitting, snapping fitting, channel locking fitting, pressure fitting, Luer locking fitting and filament ties.

15. The apparatus of claim 4, further comprising a deployable device wherein the deployable device comprises a heart assist device or cardiac compression device.

16. The apparatus of claim 15, wherein the deployable device is adapted to be preloaded inside the insertion tube.

17. The apparatus of claim 15, further comprising a deploying mechanism adapted to deploy and retract the deployable device through the insertion tube and insertion aperture member.

18. The apparatus of claim 15, wherein the insertion tube is adapted to be removed from the insertion aperture member after deployment of the deployable device.

19. The apparatus of claim 4, wherein the insertion tube comprises at least an inner concentric tube and an outer concentric tube wherein the inner concentric tube is longer than the outer concentric tube to allow attachment to the insertion aperture member wherein the insertion tube and the insertion aperture member form a hollow tube.

20. The apparatus of claim 4, wherein the upper ring of the insertion aperture member ranges in diameter from one half inch to three inches and the lower flange of the insertion aperture member ranges in diameter from one inch to five inches.

* * * * *